United States Patent [19]

Sakano et al.

[11] Patent Number: 4,490,393

[45] Date of Patent: Dec. 25, 1984

[54] THIAZOLYLUREA DERIVATIVES, A PROCESS FOR PREPARING SAME AND A PHARMACEUTICAL COMPOSITION CONTAINING SAME

[75] Inventors: Isao Sakano; Tatsuro Yokoyama; Seitaro Kajiya, all of Yokohama; Tamotsu Minami, Yokosuka; Yutaka Okazaki, Mobara; Hiroshi Tokuda, Mobara; Hiroshi Kawazura, Mobara; Mikio Kumakura, Mobara; Takuo Nakano; Akira Awaya, both of Yokohama, all of Japan

[73] Assignee: Mitsui Toatsu Kagaki Kabushiki Kaisha, Tokyo, Japan

[21] Appl. No.: 420,260

[22] PCT Filed: Jan. 21, 1982

[86] PCT No.: PCT/JP82/00021

§ 371 Date: Sep. 17, 1982

§ 102(e) Date: Sep. 17, 1982

[87] PCT Pub. No.: WO82/02553

PCT Pub. Date: Aug. 5, 1982

[30] Foreign Application Priority Data

Jan. 21, 1981 [JP] Japan .................. 56-6320

[51] Int. Cl.$^3$ .................. C07D 277/46; C07D 417/12; A61K 31/425; A61K 31/44
[52] U.S. Cl. ........................ 424/263; 424/270; 546/280; 548/196
[58] Field of Search .............. 546/280; 548/196; 424/263, 270

[56] References Cited

U.S. PATENT DOCUMENTS 4,027,031 5/1977 DeBaun et al. ............... 424/270
4,217,355 8/1980 Harbert et al. ............... 424/270
4,225,610 9/1980 Tarayre et al. ............... 424/270

FOREIGN PATENT DOCUMENTS 47-29531 11/1972 Japan .
52-125164 10/1977 Japan .
54-61172 5/1979 Japan .
54-160369 12/1979 Japan .
54-154764 12/1979 Japan .

OTHER PUBLICATIONS

Sandler et al., Organic Functional Group Preparations, pp. 142–145 (1971).
Saikachi et al., Yakugakv Zasshi 88 (1189) 1968.

Primary Examiner—Robert Gerstl
Attorney, Agent, or Firm—Birch, Stewart, Kolasch & Birch

[57] ABSTRACT

The present invention provides thiazolyl derivatives as new chemical substance represented by the general formula:

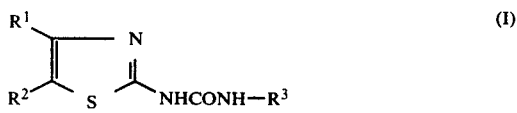

(I)

wherein $R^1$ stands for a lower alkyl group or a substituted or unsubstituted phenyl group, $R^2$ for a hydrogen atom, a lower alkyl, lower alkoxy or lower alkylthio group, and $R^3$ for a pyridyl or iso-oxazolyl group or a grouping of the general formula:

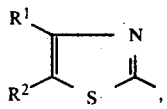

processes for preparing same and pharmaceutical compositions containing the thiazolyl derivatives. More particularly, the present invention provides new thiazolyl derivatives which possess immuno-modulating activity and are thus therapeutically effective against immunodiseases such as chronic rheumatoid arthritis and also useful against viral diseases or for the immunotherapy of cancers and possess properties desirous as medicines with a slight toxicity, processes for preparing same and pharmaceutical compositions containing the new substance.

16 Claims, No Drawings

THIAZOLYLUREA DERIVATIVES, A PROCESS FOR PREPARING SAME AND A PHARMACEUTICAL COMPOSITION CONTAINING SAME

FIELD OF THE INVENTION

This invention relates to novel thiazolylurea derivatives, processes for preparing same and medicinal compositions containing same.

More particularly, this invention relates to thiazolylurea derivatives which possess immuno-modulating activity and are thus therapeutically effective against immunodiseases such as chronic rheumatoid arthritis and are also useful against viral diseases or for the immunotherapy of cancers, processes for preparing same and medicinal compositions containing same.

A number of steroid-type and nonsteroid-type anti-inflammatory drugs have heretofore been clinically employed against autoimmune diseases such as rheumatism. However, these drugs are not quite satisfactory in their pharmacological effects, side effects and toxicity. The present inventors have carried out an extensive research on chemical substances, which give a peculiar effect to cells that take part in an immunity response and act to modulate the immunity response of the host. As a result, they have succeeded in obtaining thiazolylurea derivatives which are extremely desirous as medicines having excellent immuno-modulating activity but little toxicity.

DISCLOSURE OF INVENTION

The present invention provides thiazolylurea derivatives as new chemical substances which are represented by the general formula:

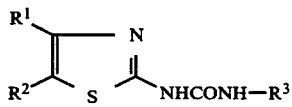
(I)

wherein $R^1$ stands for a lower alkyl group or a substituted or unsubstituted phenyl group, $R^2$ for a hydrogen atom, a lower alkyl, lower alkoxy or lower alkylthio group, and $R^3$ for a pyridyl or iso-oxazolyl group or a grouping of the general formula:

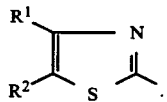

Illustrative of the representative compounds of the thiazolyl derivatives represented by the above general formula (I) in connection with the present invention are as follows:

N,N'-bis(4-methylthiazol-2-yl)urea;
N,N'-bis(4-methyl-5-methylthiazol-2-yl)urea;
N,N'-bis[4-methyl-5-(n-propyl)thiazol-2-yl]urea;
N,N'-bis(4-phenylthiazol-2-yl)urea;
N,N'-bis[4-(p-methylphenyl)thiazol-2-yl]urea;
N,N'-bis[4-(m-methylphenyl)thiazol-2-yl]urea;
N,N'-bis[4-(o-methylphenyl)thiazol-2-yl]urea;
N,N'-bis[4-(p-chlorophenyl)thiazol-2-yl]urea;
N,N'-bis[4-(m-chlorophenyl)thiazol-2-yl]urea;
N,N'-bis[4-(o-chlorophenyl)thiazol-2-yl]urea;
N,N'-bis[4-(p-methoxyphenyl)thiazol-2-yl]urea;
N,N'-bis[4-(m-methoxyphenyl)thiazol-2-yl]urea;
N,N'-bis[4-(o-methoxyphenyl)thiazol-2-yl]urea;
N,N'-bis[4-(p-nitrophenyl)thiazol-2-yl]urea;
N,N'-bis[4-(m-nitrophenyl)thiazol-2-yl]urea;
N,N'-bis[4-(o-nitrophenyl)thiazol-2-yl]urea;
N,N'-bis(5-methyl-4-phenylthiazol-2-yl)urea;
N,N'-bis(5-methoxy-4-phenylthiazol-2-yl)urea;
N,N'-bis(5-methylthio-4-phenylthiazol-2-yl)urea;
N,N'-bis[4-(p-fluorophenyl)thiazol-2-yl]urea;
N,N'-bis[4-(m-fluorophenyl)thiazol-2-yl]urea;
N,N'-bis[4-(o-fluorophenyl)thiazol-2-yl]urea;
N,N'-bis[4-(p-dimethylaminophenyl)thiazol-2-yl]urea;
N,N'-bis[4-(m-dimethylaminophenyl)thiazol-2-yl]urea;
N,N'-bis[4-(o-dimethylaminophenyl)thiazol-2-yl]urea;
N,N'-bis[4-(p-methylthiophenyl)thiazol-2-yl]urea;
N,N'-bis[4-(m-methylthiophenyl)thiazol-2-yl]urea;
N,N'-bis[4-(o-methylthiophenyl)thiazol-2-yl]urea;
N-(2-pyridyl)-N'-(4-phenylthiazol-2-yl)urea;
N-(3-pyridyl)-N'-(4-phenylthiazol-2-yl)urea;
N-(4-pyridyl)-N'-(4-phenylthiazol-2-yl)urea; and
N-(5-methylisoxazol-2-yl)-N'-(4-phenylthiazol-2-yl)urea.

As the new compounds of the present invention show tautomerism between their amine-form and their imine-form, the compounds of the present invention include all of these tautomers.

A first process provided by the present invention to prepare the novel compounds of this invention is characterized by reacting a 2-aminothiazole having the general formula:

(II)

wherein $R^1$ and $R^2$ have the same meanings as defined above, with phosgene or a chloroformate represented by the general formula:

(III)

wherein X stands for a chlorine atom or a lower alkoxy group, a benzyloxy group or a substituted or unsubstituted phenoxy group. The reaction can be carried out by either dissolving or suspending a starting material represented by the general formula (II), which may optionally be in the form of a suitable acid addition salt in a solvent, and then adding dropwise or in a similar manner a compound of the general formula (III) to the solution or suspension. Utilizable solvents include, for example, benzene, toluene, xylene, dioxane, 1,2-dimethoxyethane, tetrahydrofuran, and N,N-dimethylformamide. For the purpose of removing hydrogen chloride which will be produced in the course of the reaction, it may be possible to use an organic base such as pyridine or triethylamine or an inorganic base such as sodium carbonate, potassium carbonate or sodium hydrogen carbonate.

This reaction may proceed at temperatures below room temperature. However, it is possible to heat the reaction mixture to a temperature in the range of from room temperature to the boiling point of the solvent to accelerate the reaction.

The 2-aminothiazoles represented by the general formula (II) as starting materials are known compounds and are described in detail, for example, in technical publications [Jacques V. Metzger, ed. "The Chemistry of Heterocyclic Compounds", Vol. 34; "Thiazole and Its Derivatives", Part Two, (1979)].

The present invention also provides as a process for preparing the novel compounds represented by the general formula (I) a method in which an N-thiazolylcarbamate represented by the general formula:

(IV)

wherein $R^1$ and $R^2$ have the same definitions as given above and R stands for a lower alkyl group, a benzyl group or a substituted or unsubstituted phenyl group, is reacted with an amine having the general formula:

(V)

wherein $R^3$ has the same meaning as defined above. This reaction can generally be carried out by mixing two starting compounds respectively represented by the general formulas (IV) and (V) in a solvent such as tetrahydrofuran, dioxane, benzene, xylene, 1,2-dimethoxyethane or N,N-dimethylformamide. The reaction temperature may be chosen at will within a temperature range of from room temperature to the boiling point of the solvent. The reaction is usually completed in 1–10 hours.

The latter method is particularly advantageous for the preparation of thiazolylurea derivatives of the general formula (I) in which $R^3$ is other than thiazolyl group.

The above compounds represented by the general formula (I) have valuable pharmacological activity. It is worthy to mention specially that these compounds have excellent immuno-modulating activity. Since they have a low degree of toxicity, they are extremely useful as medicines.

The pharmacological activity of the compounds of the present invention was confirmed as follows.

Various test systems using animals have been routinely adopted for the determination of immunomodulating activity. Results of reinforcement tests of the delayed hypersensitivity, which are considered to be the most representative ones among such known test systems, will hereinafter be described as follows.

The delayed hypersensitivity induced on a mouse when picryl chloride(2-chloro-1,3,5-trinitrobenzene) is coated on the skin of the mouse is known as a typical cellular immunity. This is one of the test systems commonly adopted throughout the world [see Asherson, G. L. and Ptak, W. "Contact and Delayed Hypersensitivity in the Mouse - I. Active Sensitization and Passive Transfer", Immunology, 15, 405–416 (1968)].

This test system was used for the reinforcement tests of the delayed hypersensitivity.

Test Example 1—Reinforcement Test of Delayed Hypersensitivity

Test Procedures:

Groups of eight ICR male mice, each having a body weight of about 30 g or so, were used for the test.

Sensitization was effected by coating a 3% solution of picryl chloride in a 4/1 mixture of olive oil and acetone on the shaved abdomen of each of the mice.

Simultaneously with the sensitization, a solution or suspension of a compound of the present invention dissolved or suspended in a 0.2% solution of carboxymethylcellulose in a physiological saline was orally administered to the mouse at a dose of 50 mg per Kg of its body weight. To each mouse of a control group, was similarly administered a 0.2% carboxymethylcellulose solution in a physiological saline.

The delayed hypersensitivity was induced 7 days after the sensitization by pinching each of the pinnae of each mouse with a pair of forceps whose tip portions were wrapped with a felt impregnated with a 1% solution of picryl chloride in olive oil and coating the pinnae with the solution. The thickness of each pinna was measured before the challenging and 24 hours after the challenging and the ratio of increase of the thickness (average value of both of the pinnae of the eight mice) is shown in Table 1.

For comparison, a similar test was carried out using Levamisole hydrochloride. The results thereof are also shown.

F.t tests were carried out on the thus-obtained test results. Any group in which the test results were superior to those of the control group at significance levels of $P<0.05$ and $P<0.01$ are marked by an asterisk(*) and double asterisks(**) respectively.

Results:

When the compound of the present invention was administered simultaneously with sensitization, the delayed hypersensitivity caused by a challenging was reinforced. The reinforcement effect of the compound of the present invention was recognized to be comparable with or higher than that attained by Levamisole which was used as a comparison compound.

Thus, it is considered that the compounds of the present invention have an effect of modulating the cellular immunity response (immuno-modulating activity) in mice.

TABLE 1

Reinforcement Tests of Delayed Hypersensitivity

| Compound | Ratio of Increase of Pinna Thickness (%) |
|---|---|
| Ph-CH=C(S-)(N=)C(NHCONH-)=N(-S)C=CH-Ph (bis-phenyl thiazole urea) | 37.5* |
| bis(4-methylphenyl) analog | 36.1** |
| bis(4-methoxyphenyl) analog | 31.7* |
| bis(phenyl, SCH₃-substituted) analog | 29.0 |
| phenyl thiazole-NHCONH-isoxazole(CH₃) | 37.8** |
| phenyl thiazole-NHCONH-pyridyl | 25.4 |
| Levamisole·HCl | 31.2* |

The adjuvant arthritis in rats caused by the injection of a Mycobacterium tuberculosis adjuvant is often utilized for a model test of chronic rheumatoid arthritis in human.

The mechanism of manifestation of this disease has not completely been elucidated, but it is known that cellular immunity plays an important role. The immuno-modulating activity of the compounds of the present invention was investigated in accordance with this known adjuvant arthritis test.

Test Example 2—Adjuvant Arthritis Test (Table 2)

Test Procedures:

8-Week-old SD male rats were used for the test. In 0.1 ml of fluid paraffin, 0.4 mg of dry dead cells of Mycobacterium tuberculosis were suspended, and the suspension was injected under the heel skin of the right hind leg of each rat. Each of the compounds of the present invention was subcutaneously administered 9 times in total before and after the injection of the adjuvant. Each of the compounds of the present invention was dissolved or suspended in a 0.2% solution of carboxymethylcellulose in physiological saline and administered to each rat at a dose of 5 mg per Kg of the body weight. The swollen volume of the left hind leg was measured during the period of from the day of injection to the day of completion of the test, and the swelling ratio was calculated. For comparison, a similar test was conducted using Levamisole hydrochloride. F.t tests were carried out on the test results obtained. Any group in which the test results were superior to those of a control group administered with a 0.2% solution of carboxymethylcellulose in physiological saline at significance levels of $P<0.05$ and $P<0.01$ is marked by an asterisk (*) and double asterisks(**), respectively.

Results:

The secondary inflammation of the adjuvant arthritis was remarkably suppressed by the compounds of the present invention. The effects thereof were statistically significant over the control group.

It was recognized that the compounds of the invention comparative with or stronger than that of Levamisole used for comparison. Thus, the compounds of the present invention are considered to have immunomodulating activity and anti-arthritic activity.

Test Example 3—Acute Toxicity Test through Oral Administration

Test Procedures:

To each of a group of five ddY male mice, was orally administered a medicine dissolved or suspended in physiological saline. The animals were observed for 7 days after the administration and an estimated $LD_{50}$ value was obtained.

Results:

The estimated $LD_{50}$ value of the effective ingredient of a medicine according to this invention was 1,000 mg/Kg or higher. This value is far greater than the estimated $LD_{50}$ value of Levamisole.HCl, the latter value ranging 200–300 mg/Kg. Therefore, the toxicity of the compound of the present invention is considered to be low.

TABLE 2

Adjuvant Arthritis Test

| Compound to be tested (shown by formula) | Number of cases | Swell suppression ratio to control group (%) (average value from 16th to 20th days) |
|---|---|---|
| [structure: phenyl-thiazole-NHCONH-thiazole-phenyl] | 10 | 35.7* |
| [structure: CH₃-phenyl-thiazole-NHCONH-thiazole-phenyl-CH₃] | 10 | 29.3* |
| [structure: CH₃O-phenyl-thiazole-NHCONH-thiazole-phenyl-OCH₃] | 10 | 37.5** |
| [structure: CH₃S-...-thiazole-NHCONH-thiazole-...-SCH₃ with phenyls] | 10 | 28.8* |
| [structure: phenyl-thiazole-NHCONH-isoxazole-CH₃] | 10 | 26.6 |
| [structure: phenyl-thiazole-NHCONH-pyridyl] | 10 | 34.6* |
| Levamisole.HCl | 44 | 19.8* |

As illustrated in Tests 1 and 2, the compounds of this invention have excellent immuno-modualting activity. Thus, they are effective for the remedy of diseases accompanied by reduction or abnormal change of immune functions, for example, autoimmune diseases such as chronic rheumatoid arthritis.

A toxicity test on the effective ingredients of certain medicines according to this invention will now be described below as Test 3.

Although the compounds of this invention may be used in the form of their free base as a raw material for preparing a medicinal composition when the compounds are applied as a medicine, it is also possible to use the compounds as a pharmaceutically acceptable salt thereof.

The medicine according to this invention may be administered in the same preparation form and by the same administration method as conventional immuno-modulating agents and carcinostatic substances. For instance, as an orally administrable preparation, it may be used in the form of capsules, granules, pills, fine grains, tablets or syrup. For administering through the rectum, it is suitable to prepare the medicine into suppositories. For injection, it may be applied subcutaneously, intramuscularly or intravenously.

As diseases to which an immuno-modulating activity of the new compounds of this invention can be applied, there may be mentioned diseases accompanied by an abnormal change of immune functions, for example, chronic rheumatoid arthritis; autoimmune diseases such as polymyositis; various infectious diseases; and a wide variety of cancers. It is expected that the immuno-modulating agent of the present invention would normalize the immune functions of patients affected by such diseases.

It is desirous to choose a suitable administration method and an appropriate preparation form for a medicine according to this invention depending on the type of disease and conditions of each patient. In case of oral administration, the dose of the compound of the present invention is 0.5 to 100 mg, preferably 1 to 30 mg per Kg of the body weight per day. In case of administration to the rectum, the dose is suitably 1 to 100 mg per Kg of the body weight per day, while, in case of intravenous administration, the dose is preferably 1 to 10 mg per Kg of the body weight per day. Where it is administered subcutaneously or intramuscularly, the dose of the compound of the present invention is preferably 1 to 30 mg per Kg of the body weight per day. It is preferred that these doses be appropriately adjusted according to the type of diseases and the conditions of each patient. The therapeutic effect of the effective ingredient of the present invention may be increased, depending on the type of disease and the conditions of a patient, by using other medicines in combination. For example, when chemotherapeutic agents for cancers, such as alkylating agents and antimetabolic, which have a side effect of reducing the immunizing capacity of patients, are administered, the manifestation of such side effect may be prevented and their therapeutic effect may be synergistically increased if the effective ingredient of the present invention is used in combination.

Examples of this invention will hereinafter be described.

EXAMPLE 1

Into 50 ml of a dry pyridine solution containing 7.5 g of 2-amino-4-phenylthiazole, 4.8 g of phosgene was absorbed under cooling (about 5° C.). The temperature of the mixture was then allowed to rise to room temperature. To this solution, 7.5 g of 2-amino-4-phenyl-thiazole was added further. The mixture was stirred overnight. The pyridine was removed under reduced pressure and the residue was converted to powder in methyl alcohol. The powder was then recrystallized from an N,N-dimethylformamide/methyl alcohol mixed solvent to obtain 8.5 g of N,N'-bis(4-phenyl-thiazol-2-yl)urea.

Melting point: 285°–287° C.

Elementary analysis values as $C_{19}H_{14}N_4OS_2$:

|  | C | H | N | S |
|---|---|---|---|---|
| Calc. (%) | 60.30 | 3.73 | 14.80 | 16.92 |
| Found (%) | 60.42 | 3.76 | 14.98 | 16.87 |

IR, $\nu_{max}^{KBr}$(cm−): 3330, 3200, 3100, 1720, 1705, 1670, 1590, 1570, 1540, 1500, 1450, 1340, 1310, 1270, 1190, 1080, 910, 865, 830, 780, 710.

NMR, $\delta_{TMS}^{DMSO-d6}$(ppm): 7.2–8.0(10 H, m), 7.57(2 H, s), 10–11 (2 H, bs: disappeared with D$_2$O).

EXAMPLE 2

In 50 ml of tetrahydrofuran, was dissolved 5.7 g of 2-amino-4-p-methylphenylthiazole. The solution was cooled to 0°–5° C., followed by addition of 2.6 g of ethyl chloroformate and 2.6 g of triethylamine. The mixture was stirred at room temperature for 1 hour and then for 2 hours at the reflux temperature of tetrahydrofuran. And insoluble matter was removed from the reaction mixture through filtration. The filtrate was concentrated under reduced pressure and the residue was crystallized using N,N-dimethylformamide to obtain 2.5 g of N,N'-bis[4-(p-methylphenyl)thiazol-2-yl]urea.

Melting point: above 300° C.

Elementary analysis values as $C_{21}H_{18}N_4OS_2$:

|  | C | H | N | S |
|---|---|---|---|---|
| Calc. (%) | 62.04 | 4.46 | 13.78 | 15.78 |
| Found (%) | 62.14 | 4.43 | 13.85 | 16.08 |

NMR, $\delta_{TMS}^{DMSO-d6}$(ppm): 2.34(6 H, s), 7.2–7.8(8 H, m), 7.48(2 H, s), 10.8(2 H, bs: disappeared with D$_2$O).

EXAMPLE 3

Into 45 ml of o-xylene, were added 1.5 g of ethyl N-(4-phenyl-2-thiazolyl)carbamate and 4.0 g of 2-aminopyridine. The mixture was stirred for 2.5 hours under refluxing. The reaction solution was allowed to stand for cooling. Deposited crystals were collected by filtration and washed with methyl alcohol. The crystals were then recrystallized from an N,N-dimethylformamide/methyl alcohol mixed solvent to obtain 1.2 g of N-(2-pyridyl)-N'-(4-phenylthiazol-2-yl)urea.

Melting point: 247°–249° C.

Elementary analysis values as $C_{15}H_{12}N_4OS$:

|  | C | H | N | S |
|---|---|---|---|---|
| Calc. (%) | 60.79 | 4.08 | 18.90 | 10.82 |
| Found (%) | 60.66 | 3.92 | 18.82 | 10.81 |

NMR, $\delta_{TMS}^{DMSO-d6}$(ppm): 7.0–8.0(9 H, m), 8.39(1 H, d), 9.92(1 H, s), 12.22(1 H, s: disappeared with D$_2$O).

Following the procedures of Examples 1–3, the compounds of the following examples were obtained from their corresponding starting materials.

EXAMPLE 4

N,N'-Bis[4-(p-methoxyphenyl)thiazol-2-yl]urea

Melting point: 288°–292° C.

Elementary analysis values as $C_{21}H_{18}N_4O_3S_2$:

|  | C | H | N | S |
|---|---|---|---|---|
| Calc. (%) | 57.52 | 4.14 | 12.78 | 14.62 |
| Found (%) | 57.42 | 4.09 | 12.72 | 14.67 |

NMR, $\delta_{TMS}^{DMSO-d6}$(ppm): 3.8(6 H, s), 7.0–7.8(8 H, m), 7.4(2 H, s).

EXAMPLE 5

N,N'-Bis[4-(p-chlorophenyl)thiazol-2-yl]urea

Melting point: 290°–300° C.
Elementary analysis values as $C_{19}H_{12}Cl_2N_4OS_2$:

|  | C | H | Cl | N | S |
|---|---|---|---|---|---|
| Calc. (%) | 51.01 | 2.70 | 15.85 | 12.52 | 14.33 |
| Found (%) | 51.06 | 2.63 | 15.83 | 12.37 | 14.37 |

NMR, $\delta_{TMS}^{DMSO-d6}$(ppm): 7.45(4 H, d), 7.63(2 H, s), 7.90(4 H, s), 10.84(2 H, bs: disappeared with $D_2O$).

EXAMPLE 6

N,N'-Bis[4-methyl-5-(n-propyl)thiazol-2-yl]urea

Melting point: 273.5°–274.5° C.
Elementary analysis values as $C_{15}H_{22}N_4OS_2$:

|  | C | H | N | S |
|---|---|---|---|---|
| Calc. (%) | 53.22 | 6.55 | 16.55 | 18.95 |
| Found (%) | 53.47 | 6.58 | 16.56 | 18.86 |

EXAMPLE 7

N,N'-Bis[5-methyl-4-phenylthiazol-2-yl]urea

Melting point: 254°–256° C.
Elementary analysis values as $C_{21}H_{18}N_4OS_2$:

|  | C | H | N | S |
|---|---|---|---|---|
| Calc. (%) | 62.04 | 4.46 | 13.78 | 15.78 |
| Found (%) | 61.94 | 4.49 | 14.00 | 15.71 |

NMR, $\delta_{TMS}^{DMSO-d6}$(ppm): 2.50(6 H, s), 7.35–7.65(12 H, m).

EXAMPLE 8

N,N'-Bis[5-methylthio-4-phenylthiazol-2-yl]urea

Melting point: 207–210° C.
Elementary analysis values as $C_{21}H_{18}N_4O_4S_2$:

|  | C | H | N | S |
|---|---|---|---|---|
| Calc. (%) | 53.59 | 3.85 | 11.90 | 27.25 |
| Found (%) | 53.62 | 4.01 | 11.76 | 27.24 |

EXAMPLE 9

N-(5-methylisoxazol-2-yl)-N'-(4-phenylthiazol-2-yl)urea

Melting point: 212°–220° C.
Elementary analysis values as $C_{14}H_{12}N_4O_2S$:

|  | C | H | N | S |
|---|---|---|---|---|
| Calc. (%) | 55.99 | 4.03 | 18.65 | 10.68 |
| Found (%) | 56.01 | 4.07 | 18.75 | 10.62 |

NMR, $\delta_{TMS}^{DMSO-d6}$(ppm): 2.4(3 H, s), 6.62(1 H, s), 7.3–7.6(5 H, m), 7.93(1 H, d), 9.74(1 H, s), 10.70(1 H, s: disappeared with $D_2O$).

EXAMPLE 10

N,N'-Bis[4-(m-chlorophenyl)thiazol-2-yl]urea

Melting point: 265°–268° C.
Elementary analysis values as $C_{19}H_{12}Cl_2N_4OS_2$:

|  | C | H | Cl | N | S |
|---|---|---|---|---|---|
| Calc. (%) | 51.01 | 2.70 | 15.85 | 12.52 | 14.33 |
| Found (%) | 50.84 | 2.84 | 15.79 | 12.32 | 14.01 |

NMR, $\delta_{TMS}^{DMSO-d6}$(ppm) 7.6–8.2(10 H, m), 11.32(2 H, br: disappeared with $D_2O$).

EXAMPLE 11

N,N'-Bis[4-(m-methylphenyl)thiazol-2-yl]urea

Melting point: 254°–256° C.
Elementary analysis values as $C_{21}H_{12}N_4OS_2$:

|  | C | H | N | S |
|---|---|---|---|---|
| Calc. (%) | 62.98 | 3.02 | 13.99 | 16.01 |
| Found (%) | 62.55 | 3.13 | 13.57 | 15.81 |

NMR, $\delta_{TMS}^{DMSO-d6}$(ppm): 2.40(6 H, s), 7.1–7.8(10 H, m), 11.0(2 H, br: disappeared with $D_2O$).

EXAMPLE 12

N,N'-Bis[4-(m-nitrophenyl)thiazol-2-yl]urea

Melting point: 273°–276° C.
Elementary analysis values as $C_{19}H_{12}N_6O_5S_2$:

|  | C | H | N | S |
|---|---|---|---|---|
| Calc. (%) | 48.71 | 2.58 | 17.94 | 13.69 |
| Found (%) | 48.71 | 2.48 | 17.70 | 13.48 |

EXAMPLE 13

N,N'-Bis[4-(p-fluorophenyl)thiazol-2-yl]urea

Melting point: 229°–302° C.
Elementary analysis value as $C_{19}H_{12}F_2N_4OS_2$:

|  | C | H | F | N | S |
|---|---|---|---|---|---|
| Calc. (%) | 55.06 | 2.92 | 9.17 | 13.52 | 15.47 |
| Found (%) | 54.93 | 2.81 | 9.29 | 13.47 | 15.27 |

NMR, $\delta_{TMS}^{DMSO-d6}$(ppm): 7.2–8.2(8 H, m), 7.68(2 H, s), 11.0(2 H, br; disappeared with $D_2O$).

EXAMPLE 14

N,N'-Bis[4-(p-dimethylaminophenyl)thiazol-2-yl]urea

Melting point: 263°–266° C. (decomp.).
Elementary analysis value as $C_{23}H_{24}N_6OS_2$:

|  | C | H | N | S |
|---|---|---|---|---|
| Calc. (%) | 59.46 | 5.21 | 18.09 | 13.80 |
| Found (%) | 59.39 | 5.22 | 17.94 | 13.85 |

EXAMPLE 15

N,N'-Bis[4-(p-methylthiophenyl)thiazol-2-yl]urea

Melting point: 283°–284.5° C.

Elementary analysis value as $C_{21}H_{18}N_4OS_2$:

|  | C | H | N | S |
|---|---|---|---|---|
| Calc. (%) | 53.59 | 3.85 | 11.90 | 27.25 |
| Found (%) | 35.62 | 3.75 | 11.88 | 26.95 |

NMR, $\delta_{TMS}^{DMSO-d6}$(ppm): 2.52(6 H, s), 7.54(2 H, s), 7.24–7.92 (8 H, m), 10.90(2 H, br: disappeared with $D_2O$).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. Thiazolylurea derivatives of the formula:

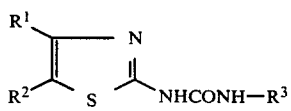

wherein $R^1$ stands for a lower alkyl group, a phenyl group or a phenyl group substituted with a lower alkyl group, a lower alkoxy group, a lower alkylthio group, a lower alkylamino group, a halogen atom or a nitro group, $R^2$ for a hydrogen atom, a lower alkyl, alkoxy or alkylthio group, and $R^3$ for a pyridyl group, an isooxazolyl group or a grouping of the general formula:

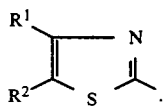

2. A thiazolylurea derivative according to claim 1, wherein, in the above formula (I), $R^1$ is a phenyl group or a phenyl group substituted with a lower alkyl group, a lower alkoxy group, a lower alkylthio group, a lower alkylamino group, a halogen atom or a nitro group, $R^2$ is a hydrogen atom and $R^3$ is a 2-pyridyl group, a 5-methyl-2-oxazolyl group or a grouping of the general formula:

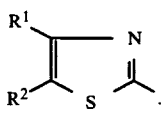

3. A pharmaceutical composition possessing immunomodulating activity, characterized by containing as an effective ingredient a thiazolylurea derivative of the formula:

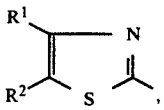

wherein $R^1$ stands for a lower alkyl group, a phenyl group or a phenyl group substituted with a lower alkyl group, a lower alkoxy group, a lower alkylthio group, a lower alkylamino group, a halogen atom or a nitro group, $R^2$ for a hydrogen atom or a lower alkyl, alkoxy or alkylthio group, and $R^3$ for a pyridyl group, an isooxazolyl group or a grouping of the general formula:

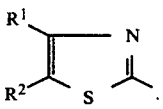

or a pharmaceutically acceptable salt thereof together with a pharmaceutically acceptable carrier diluent.

4. A pharmaceutical composition possessing immunomodulating activity according to claim 3, wherein in the formula (I) $R^1$ is a phenyl group or a phenyl group substituted with a lower alkyl group, a lower alkoxy group, a lower alkylthio group, a lower alkylamino group, a halogen atom or a nitro group, $R^2$ is a hydrogen atom and $R^3$ is a 2-pyridyl group, a 5-methyl-2-oxazolyl group or a grouping of the general formula:

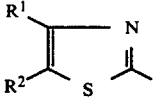

5. A method for treating chronic rheumatoid arthritis comprising administering an effective anti-arthritic amount of a thiazolyl derivative according to claim 1.

6. A pharmaceutically acceptable salt of a thiazolylurea derivative according to claim 1.

7. A pharmaceutically acceptable salt of a theazolylurea derivative according to claim 2.

8. A thiazolylurea derivative according to claim 1, wherein $R^1$ is phenyl or p-methylphenyl, $R^2$ is hydrogen or —$SCH_3$, and $R^3$ is a member selected from the group consisting of

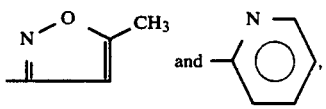

wherein $R^1$ and $R^2$ are defined as above,

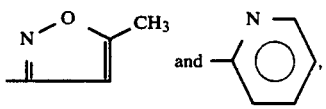

or tautomers thereof.

9. A pharmaceutically acceptable salt of a thiazolylurea derivative according to claim 8.

10. A pharmaceutical composition according to claim 3, wherein in the formula (I) $R^1$ is phenyl or p-methylphenyl, $R^2$ is hydrogen or $-SCH_3$, and $R^3$ is a member selected from the group consisting of

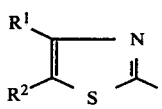

wherein $R^1$ and $R^2$ are defined as above,

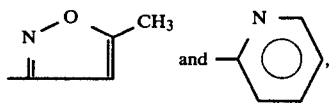

or tautomers thereof.

11. A thiazolylurea derivative according to claim 1, wherein $R^1$ is methyl, phenyl, or phenyl substituted with methyl, methoxy, chloro, fluoro, dimethylamino, or methylthio, $R^2$ is methyl, hydrogen, propyl, methoxy or methylthio and $R^3$ is a pyridyl group or a 5-methylisoxazol group, or tautomers thereof.

12. A pharmaceutically acceptable salt of a thiazolylurea derivative according to claim 11.

13. A pharmaceutical composition according to claim 3, wherein in the formula (I), $R^1$ is methyl, phenyl, or phenyl substituted with methyl, methoxy, chloro, fluoro, dimethylamino, or methylthio, $R^2$ is methyl, hydrogen, propyl, methoxy or methylthio and $R^3$ is a pyridyl group or a 5-methylisoxazolyl group, or tautomers thereof.

14. A method for treating chronic rheumatoid arthritis comprising administering an effective anti-arthritic amount of a thiazolyl derivative according to claim 2.

15. A method for treating chronic rheumatoid arthritis comprising administering an effective anti-arthritic amount of a thiazolyl derivative according to claim 8.

16. A method for treating chronic rheumatoid arthritis comprising administering an effective anti-arthritic amount of a thiazolyl derivative according to claim 11.

* * * * *